United States Patent [19]

Weikl et al.

[11] 4,451,256

[45] May 29, 1984

[54] CATHETER SET

[75] Inventors: Andreas Weikl; Max Hubmann, both of Erlangen, Fed. Rep. of Germany

[73] Assignee: Intermedicat GmbH, Switzerland

[21] Appl. No.: 372,739

[22] Filed: Apr. 28, 1982

[30] Foreign Application Priority Data

May 6, 1981 [DE] Fed. Rep. of Germany ....... 3117802

[51] Int. Cl.³ .............................................. A61M 5/00
[52] U.S. Cl. ..................................... 604/164; 128/343
[58] Field of Search ................................... 604/51–53, 604/158–170; 128/343

[56] References Cited

U.S. PATENT DOCUMENTS

| 3,370,587 | 2/1968 | Vizcarra | 604/53 |
| 3,598,112 | 8/1971 | Warren | 604/53 |
| 3,788,318 | 1/1974 | Kim et al. | 604/164 |
| 3,877,429 | 4/1975 | Rasumoff | 604/158 |
| 4,211,234 | 7/1980 | Fisher | 128/343 X |
| 4,306,562 | 12/1981 | Osborne | 604/164 X |
| 4,354,491 | 10/1982 | Marbry | 604/160 |

OTHER PUBLICATIONS

Kessel et al., "Zeitschrift fur Kardiologie" Oct. 1974, No. 10, pp. 944–949.

Primary Examiner—Dalton L. Truluck
Attorney, Agent, or Firm—Merriam, Marshall & Bicknell

[57] ABSTRACT

In order to keep the opening for inserting a catheter into a blood vessel as small as possible, a catheter insertion tube is used which coaxially surrounds the puncturing canula and consists, at least in a circumferential area and/or at least along a portion of its length, of one or several dilatable or expandable areas permitting enlargement of its internal diameter. The diameter of the catheter insertion tube, at the front end where it is inserted into the blood vessel, is approximately equal or smaller than the outer diameter of the catheter. The catheter insertion tube is expandable at least over the front or forward portion of its length by the catheter. The catheter insertion tube is removable from the puncture over the catheter while the catheter is advanced into the puncture and is tighty sealed by the catheter because the catheter has an external diameter equal to or larger than the puncture previously occupied by the insertion tube.

15 Claims, 22 Drawing Figures

CATHETER SET

This invention is concerned with a novel catheter set for inserting a catheter into a blood vessel.

BACKGROUND OF THE INVENTION

A number of catheter sets are already known. According to a construction disclosed in DE-GM 74 27 426, the catheter upon insertion, contacts and presses against the inner wall surface of a conically-shaped catheter insertion tube or sleeve. The tube is made of a polymeric synthetic material and is provided with a longitudinal tear line. The tube is split open along the tear line by the catheter pressure as it advances. Thus, the catheter insertion tube portion outside of the puncture site serves as a kind of guide channel to easily insert the catheter into the punctured blood vessel. However, this type of insertion presumes that the catheter insertion tube continues to remain in the punctured blood vessel until the following catheter also penetrates the puncture site, since the catheter insertion tube represents the sole insertion aid for the catheter. This means, however, that the puncture site must have a diameter larger by at least the wall thickness of the catheter insertion tube than is necessary for the insertion of the catheter. This enlarged size of puncture site, which is inherent in the previously known catheter set, can be even more enlarged inadvertently, due to the fact that the catheter insertion tube has to remain in the blood vessel during insertion of the catheter. Because of the splitting of the catheter insertion tube and its subsequent enlarged diameter, the puncture site is correspondingly enlarged so that one has to fear formation of blood vessel fissures at the puncture site. Consequently, as a rule it is not possible for the subsequently inserted catheter to effect an adequate seal at the blood vessel puncture site. This has lead, particularly in infants, to dangerous bleeding and side effects, in particular to infections.

SUMMARY OF THE INVENTION

The invention has, as one of its purposes, the provision of an improved catheter set and improved elements useful therein, broadly of the above mentioned type, which will not enlarge the dimensions of the puncture site beyond the outer diameter of the catheter which is to be subsequently inserted, so that a safe seal with the catheter to be inserted at the puncture site is guaranteed.

Due to the improved catheter set and improved elements incorporated therein, provided according to the invention, which includes a catheter having an outer diameter at least approximately the same or slightly larger than the outer diameter of the catheter insertion tube, as well as the fact that the catheter insertion tube consists, at least in one or several circumferential areas and/or at least along a portion of its length, one or more dilatable areas which permit an enlargement or expansion of the diameter, it is possible for the catheter insertion tube, after the catheter or the mandrin, respectively, is inserted in the puncture, to be pulled back over the catheter and thus be removed from the puncture, whereby the puncture is efficiently sealed off by means of the catheter with an equally large or slightly larger outer diameter than the cross-sectional opening of the puncture site. In particular, over-expansion of the blood vessel, or fissure of the same at or in the area of the puncture, is avoided upon insertion of the catheter.

Thus, with the catheter set according to the invention, not only a safe seal of the puncture is guaranteed, but also adverse side effects, such as the entrance of air, dirt particles or similar materials into the blood stream, are avoided to a greater extent than before.

According to one embodiment, the invention provides an improvement in a catheter set including a catheter and a catheter insertion tube into which the catheter to be inserted into a blood vessel is insertable, with the improvement comprising a catheter having an elongated front end portion with an external diameter smaller than the external diameter of the main body of the catheter; a catheter insertion tube having a front end portion with an internal diameter smaller than the external diameter of the main body of the catheter; the elongated smaller front end portion of the catheter being axially slidable in the catheter insertion tube front end portion without expanding the same; and the front end portion of the catheter insertion tube being expandable by movement of the catheter main body axially therein.

Desirably, the catheter main body external diameter is not less than the external diameter of the front end portion of the catheter insertion tube at a blood vessel puncture.

According to another embodiment of the invention, there is provided an improved catheter set including a catheter and a catheter insertion tube into which the catheter to be inserted into a blood vessel is insertable, with the improvement comprising a catheter; a catheter insertion tube having a front end portion with an internal diameter smaller than the external diameter of the catheter; the front end portion of the catheter insertion tube being expandable by movement of the catheter axially therein; and a mandrin having an outer diameter not larger than the internal diameter of the catheter insertion tube front end portion internal diameter.

Desirably, the catheter external diameter is not less than the external diameter of the front end portion of the catheter insertion tube at a blood vessel puncture.

The invention will be described in detail in conjunction with the specific embodiments illustrated by the attached greatly enlarged drawings.

DETAILED DESCRIPTION OF THE DRAWINGS

Figure 1:
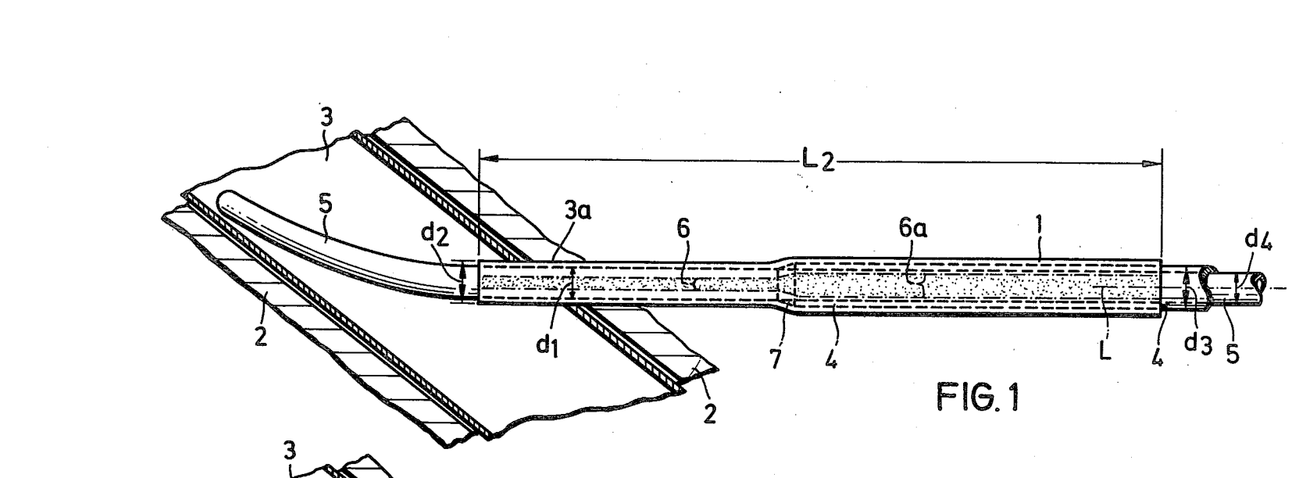
FIG. 1 is an elevational view partially in section of a catheter set according to the invention with a catheter insertion tube or sleeve having a dilatable area, parallel to the longitudinal axis, extending over its entire length, as well as with a partially inserted catheter and inserted mandrin at a blood vessel puncture site.

A catheter set according to the invention contains a conventional puncturing canula made of steel which is not illustrated in the drawing, said canula being coaxially surrounded by a catheter insertion tube 1 (FIG. 1). The tube 1 is inserted, together with the above named puncturing canula, through the skin 2 into a blood vessel 3. The puncturing canula is then entirely withdrawn by pulling it back from the catheter insertion tube 1. Thereafter the catheter 4, with the coaxial mandrin (or mandrel) 5 in place is inserted into the catheter insertion tube 1 as can be seen from FIG. 1. The catheter insertion tube 1 can be cylindrical or it can be slightly tapered conically with the smaller end to be inserted into the blood vessel 3. The inner diameter of the catheter insertion tube 1 in the vicinity of the puncture location 3a has the reference figure $d_1$, while the outer diameter of the end inserted into the blood vessel 3 is referenced with $d_2$. The outer diameter of the catheter insertion tube 1 in the vicinity of the puncture location 3a is equal, or at least almost equal, to the diameter $d_2$ at the container-side end of the catheter insertion tube 1.

The catheter insertion tube 1 over its entire length $L_2$ is provided with a dilatable area 6 running parallel to the longitudinal axis L. If necessary, several dilatable areas 6 can be distributed around the circumference of the catheter insertion tube 1.

The cylindrical or tubular catheter 4 has an outer diameter $d_3$ which is at least the same as, but preferably is a few tenths of a millimeter larger than, the outer diameter $d_2$ of the catheter insertion tube 1, or of a conical ended catheter insertion tube 1. When the front end 7 of catheter 4 is inserted into the catheter insertion tube 1 an immediate spreading or enlarging effect is obtained because the catheter 4 outer diameter $d_3$ is larger than the outer wall diameter $d_2$ of the catheter insertion tube 1. As a result, the wall of the catheter insertion tube 1 is expanded in the dilatable area(s) 6.

FIG. 1 shows the rounded forward end of catheter 4 after it has been pushed forward to approximately the middle of the catheter insertion tube 1 as illustrated by the expanded or enlarged area 6a. FIG. 1 shows that the catheter 4 with its slightly rounded front point 7 has reached approximately the center of the catheter insertion tube 1, as this is illustrated by the expanded dilatable area 6a.

The mandrin 5 has an outer diameter $d_4$ which is smaller, or approximately the same, as the inner diameter of the catheter 4. Therefore, the mandrin 5, together with the catheter 4, can be inserted into the catheter insertion tube 1 and it can be inserted into the blood vessel 3 through the catheter insertion tube 1 beyond the puncture site 3a. This can be done without stressing, with respect to expanding, the dilatable area(s) 6 of the catheter insertion tube 1 by means of the mandrin 5. The mandrin 5 has a sufficient length to be securely placed in blood vessel 3 to function as a guide element for the subsequent insertion of the catheter 4 through puncture 3a. The mandrin or mandrel 5 can be designed as a solid body or as a hollow body like the coaxial catheter 4 and preferably it is made from a sufficiently flexible synthetic polymeric material.

After the mandrin 5 has been securely placed in the blood vessel 3, the catheter insertion tube 1 is continuously pulled back or withdrawn while simultaneously the catheter 4 can be moved towards the puncture location 3a. Due to withdrawal of the catheter insertion tube 1 and, possibly, due to the simultaneous forward movement of catheter 4 which, as mentioned above, has an outer diameter $d_3$ which is preferably equal to or larger than the outer diameter $d_2$ of the catheter insertion tube 1, the dilatable area(s) 6 is or are expanded so that the catheter insertion tube 1 is withdrawn over catheter 4 and can be pulled out of the puncture site 3a. Thereafter the catheter 4, with the aid of the mandrin 5 as a guide member, is inserted completely through the skin 2 and the subcutaneous tissue into the blood vessel 3. Once the catheter 4 is positioned in the blood vessel 3, the mandrin 5 has served its purpose so that it can be removed from the blood vessel 3. Thus, only the catheter 4 remains in the blood vessel 3. The puncture 3a is tightly sealed by means of catheter 4. To facilitate insertion of catheter 4 into the blood vessel 3, the front end 7 of catheter 4 can be provided with a rounded nose or chamfering of a suitable length.

The catheter insertion tube 1 can be made cylindrical, so that its outer diameter $d_2$ approximately corresponds to the outer diameter $d_3$ of the catheter 4 and, furthermore, the catheter 4 can be provided with the chamfering mentioned above to facilitate its entry and advancement in the catheter insertion tube 1.

It is also feasible for the catheter insertion tube 1 to be shaped like a truncated cone wherein its larger opening, for the insertion of the catheter 4, corresponds at least to the outer diameter $d_2$ at the container-side end of the catheter insertion tube 1.

For fast utilization of the catheter set according to the invention, it is desirable that the mandrin 5 and the catheter 4 be designed and assembled as a structural unit or combination so that they can be inserted together into the catheter insertion tube 1.

Figure 2:
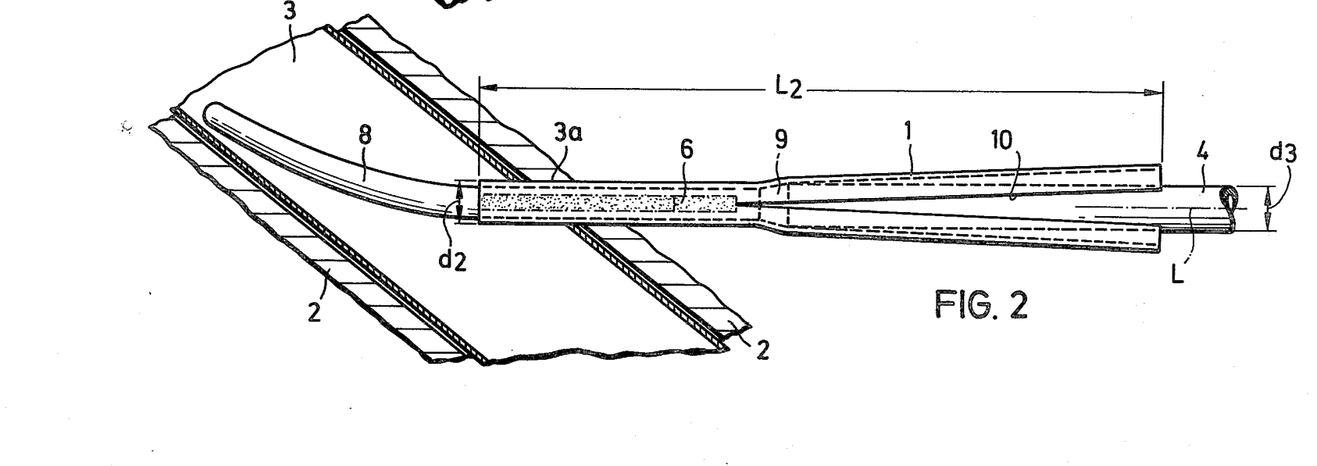
FIG. 2 is similar to FIG. 1 and shows another embodiment of a catheter set according to the invention whereby a catheter is used with a bill-shaped catheter projection of reduced diameter, and the catheter insertion tube has a dilatable area which permits an enlargement in diameter only along a portion of its length.

The embodiment of the invention illustrated in FIG. 2 differs from that of FIG. 1 in that, instead of the mandrin, a catheter 4 with a bill-like projection 8 of smaller diameter is provided. The portion 8 of catheter 4 having a smaller diameter than the remainder of the catheter 4, desirably has a length which is at least as long as, and advisably is a few centimeters longer than, the length $L_2$ of the catheter insertion tube 1 so that it can be securely placed in blood vessel 3. The reduced portion 8 ends at 9 and by means of an enlarging step or transition area it merges into the main body of catheter 4. The step or transition area serves to expand or enlarge the dilatable area(s) 6 of the catheter insertion tube 1, preferably by simultaneously pulling back the catheter insertion tube 1 and pushing the catheter forward. In this way, the catheter insertion tube 1 is pulled back over the catheter 4. Since here too the outer diameter $d_3$ of the catheter 4 is approximately equal to the outer diameter $d_2$ of the point or front end of the catheter insertion tube 1, the catheter 4 can be securely placed in the blood vessel 3 without difficulty in the same manner as illustrated above, whereby simultaneously the desired sealing effect is obtained in puncture 3a.

In the embodiment shown in FIG. 2, the catheter insertion tube 1 front portion, by the puncture 3a, has one or more dilatable areas 6. These dilatable areas extend over about one-third to one-half the length $L_2$ of tube 1. The adjoining portion of the catheter insertion tube 1 is provided with a continuous area 10 which is separable in the longitudinal direction. In this type of construction, when the catheter insertion tube 1 is pulled back over catheter 4 frictional resistance between them is reduced because the catheter insertion tube 1 separates or splits. The separated or split portion of the catheter insertion tube 1 actually can be retracted over the catheter 4 without friction.

The bill-like or trunk-type projection 8 of the catheter 4 is not necessarily designed as one piece together with the main body of catheter 4. The catheter portion 8 can be mounted on a corresponding connecting piece for the catheter 4. For example, it can be securely connected to catheter 4 by means of welding or a suitable fitting. It is also possible to insert the reduced portion 8 coaxially into the catheter 4. In this embodiment, different materials can be used for maximum benefit on the one hand for the guide member 8, and on the other hand for that part of catheter 4 which causes the catheter insertion tube 1 to expand as it is pulled back, and to seal with the puncture site 3a.

In the embodiment of FIG. 2 the bill-like extension 8 of the catheter 4 provides a particular advantage in that it has the same cross-sectional opening as the main body of catheter 4. Thus, the flow resistance is unchanged in the entire length of the catheter.

The catheter 4 and the mandrin 8 preferably are made of a non-abrasive, sufficiently flexible synthetic polymeric material to avoid, on the one hand, the unintentional removal by abrasion of even the smallest particle from the catheter and, on the other hand, to be able to place these two elements securely and without danger in the blood vessel 3.

As FIG. 2 shows, the catheter insertion tube 1 can be designed primarily cylindrically so that its outer diameter $d_2$ approximately corresponds to the outer diameter $d_3$ of the catheter 4. Furthermore, upon use of a mandrin 5 (see FIG. 1) the catheter 4 is desirably provided with chamfering of a suitable length for easy insertion into the catheter insertion tube 1.

As briefly stated in connection with FIG. 1, the catheter insertion tube 1 can be provided, along its circumference over its entire length $L_2$, with one or several discreet, dilatable areas 6. These dilatable areas 6 can consist preferably of rubber-elastic material, in particular, of elastomers or of equivalent resilient synthetic materials.

Figure 3A:
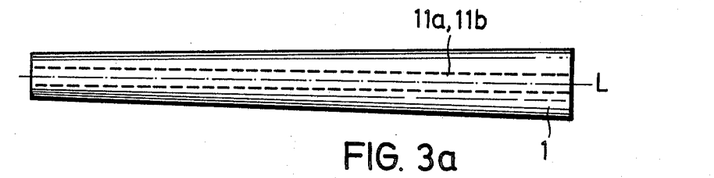
FIGS. 3a and 3b show in elevation and cross-section respectively a conical catheter insertion tube with thinner and weaker zones parallel to the longitudinal axis.
Figure 3B:
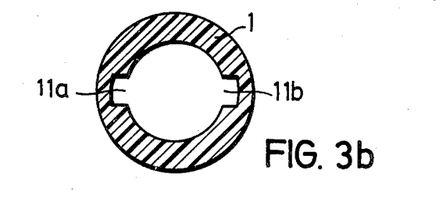

As shown in FIGS. 3a and 3b, the discrete, dilatable areas may consist of zones 11a and 11b having reduced material thickness and strength. The thinner and weaker zones 11a, 11b preferably run parallel to the longitudinal axis L and represent enlargements of the cross-sectional opening of the catheter insertion tube 1. Since the wall thickness of the catheter insertion tube 1 is small by nature and, for example, lies between 0.1 to 0.3 mm, a sufficient dilation can be readily achieved by a slight reduction of the material thickness in the zones 11a, 11b. This especially holds good for sufficiently elastic materials used for the catheter insertion tube 1.

Figures 4A, 4B:
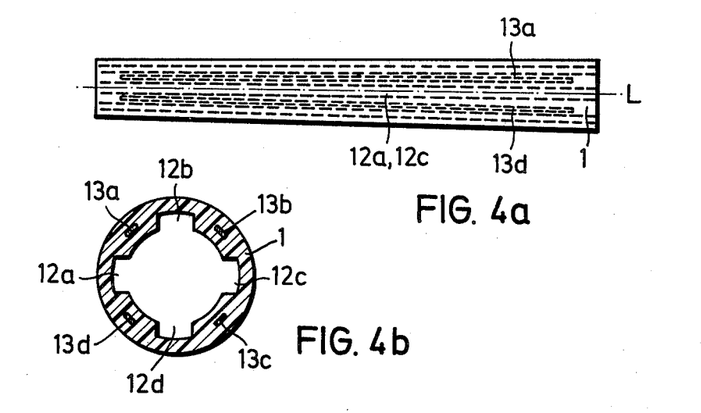
FIGS. 4a and 4b show in elevation and cross-section respectively a conical catheter insertion tube with reinforcing elements parallel to the longitudinal axis and to the thinner and weaker areas.

In order to give the catheter insertion tube 1, despite the use of an adequately elastic material, sufficient rigidity, to guarantee its secure insertion into the puncture location 3a, the catheter insertion tube 1 can be provided along its circumference with at least one, preferably several, reinforcing or stiffening elements 13a to 13d corresponding to the number of weaker portions 12a to 12d. The reinforcing elements 13a to 13d preferably run parallel to the longitudinal axis L of the catheter insertion tube 1 and preferably consist of spring material, in particular spring steel. These reinforcing elements are embedded into the materially stronger or thicker portions of the catheter insertion tube 1 during its manufacture.

Figures 5A, 5B:
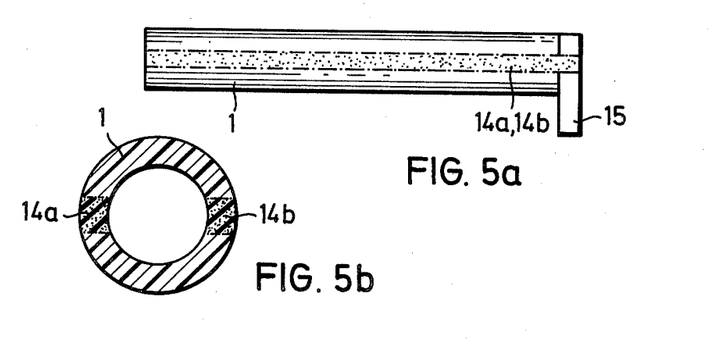
FIGS. 5a and 5b show in elevation and cross-section respectively a cylindrical catheter insertion tube with discrete dilatable areas made of elastic rubber material parallel to the longitudinal axis.

As FIGS. 5a and 5b show, the catheter insertion tube 1 can have a continuously uniform cross-section except for the dilatable areas 14a and 14b, which can be made from a material with highly elastic characteristics as, for example, silicone rubber or natural rubber. For improved guidance of the catheter insertion tube 1, the latter can be provided with a hand grip 15 at the end located away from the puncture location 3a.

As shown in FIGS. 1 and 5a, the catheter insertion tube 1 can be provided with dilatable areas which extend over the entire length $L_2$.

On the other hand, it is possible to design the catheter insertion tube 1 in such a manner that it is provided over a portion of its length only with discreet dilatable areas 6, while the remaining portion is provided with a continuous longitudinal splittable separation area 10, as this has been explained in regard to FIG. 2.

Figure 6:
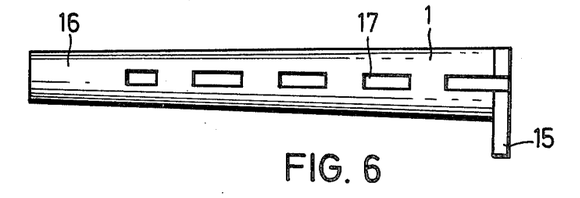
FIGS. 6 and 7 show in elevation conical catheter insertion tubes which consist only of dilatable material in the area neighboring the puncture site, and in the remaining portion of the length is provided with a splittable or continuous open tear area.
Figure 7:
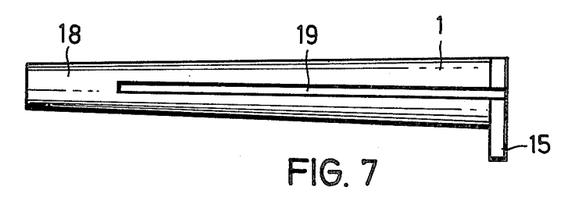

FIGS. 6 and 7 show variations of the above-described type of construction. According to FIG. 6, the end 16 of a conically tapered catheter insertion tube 1 consists of a different, particularly flexible, rubber-elastic material, while the adjoining area of the catheter insertion tube 1 is provided with a longitudinal splittable separation area 17. The material of the catheter insertion tube 1, in the area of the longitudinal separatable or dividable area 17, can be stiffer than the material of the elastically dilatable point or end 16 of the catheter insertion tube 1. In this embodiment too, the sliding resistance, upon retraction of the catheter insertion tube 1 over the catheter 4, is clearly reduced so that removal of the catheter insertion tube 1 from the puncture site 3a is entirely free of problems.

In the embodiment according to FIG. 7, the catheter insertion tube 1 is made entirely of the same material. However, this material, in the area of the point or end 18 of the catheter insertion tube 1, is made thinner than in the remaining portion. Reference number 19 refers to a longitudinal separation or dividable area which makes possible effortless splitting of the catheter insertion tube 1 in its non-weakened or stronger portion. Reference number 15 in FIGS. 6 and 7 refers to a schematically shown hand grip which, of course, is so positioned that expansion of the catheter insertion tube 1 in the splittable area 17 or in the separation area 19 is not made more difficult.

Figure 8A:
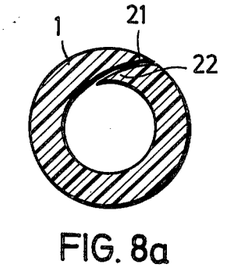
FIGS. 8a and 8b are cross-sectional views of a cylindrical catheter insertion tube with a continuous longitudinal tear area parallel to the longitudinal axis, whereby the ends or edges of the catheter insertion tube in the area of the longitudinal tear area are provided with slits, shown first in cross-section in a normal position and then in the position it is dilated to by the catheter.
Figure 8B:
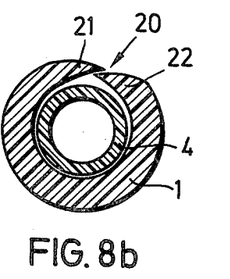

FIGS. 8a and 8b show an embodiment of the catheter insertion tube 1 with a continuous longitudinal separation area 20 parallel to the longitudinal axis L. FIG. 8a shows the catheter insertion tube 1 in its starting position without the insertable catheter 4, and FIG. 8b shows the catheter insertion tube 1 in the dilated position expanded by the inserted catheter 4. The free longitudinal or axial edges 21, 22 of the catheter insertion tube 1 are provided in the area of the longitudinal separation area 20, so that even in the dilated condition a slight overlapping of the free edges 21, 22 of the catheter insertion tube 1 is obtained.

Figure 9A:
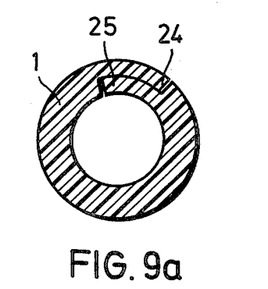
FIGS. 9a and 9b are cross-sectional views of a cylindrical catheter insertion tube with a continuous longitudinal tear area parallel to the longitudinal axis, whereby the ends or edges of the catheter insertion tube are provided with mating step-like portions, shown first in cross-section in a normal position and then in the position it is dilated to by the catheter.
Figure 9B:
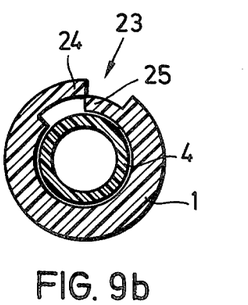

FIGS. 9a and 9b illustrate another variation of a continuous longitudinal separation area 23 running parallel to the longitudinal axis L. In this case the longitudinal or axial free edge sections 24, 25 of the catheter insertion tube 1 are provided, in the longitudinal separation area 23, with mating or cooperating overlapping step-like sections. In this embodiment too, some overlapping of the step-like sections 24, 25 continues even in the dilated or expanded condition which results upon insertion of the catheter into insertion tube 1.

The invention provides a catheter set which not only can be handled easily and securely, but which also guarantees an absolutely effective seal at the puncture site so that the numerous disadvantages which a leaking puncture causes are avoided.

The catheter set according to the invention applies the insertion set Seldinger technology, but only consists of two portions or elements to be manipulated separately, namely, the catheter insertion tube 1 and the catheter 4, or the structural unit of catheter and mandrin respectively. Thus, the manipulation of this catheter set is substantially simplified and safer than the previous sets according to the Seldinger technology. In addition, this catheter set has the advantage that aseptic conditions can be much easier maintained. Also of advantage is the possibility of combining a catheter set according to the invention with an automatically closing and locking catheter connection head so that a complete one-piece set, according to the Seldinger technology, can be obtained.

Figures 10, 11:
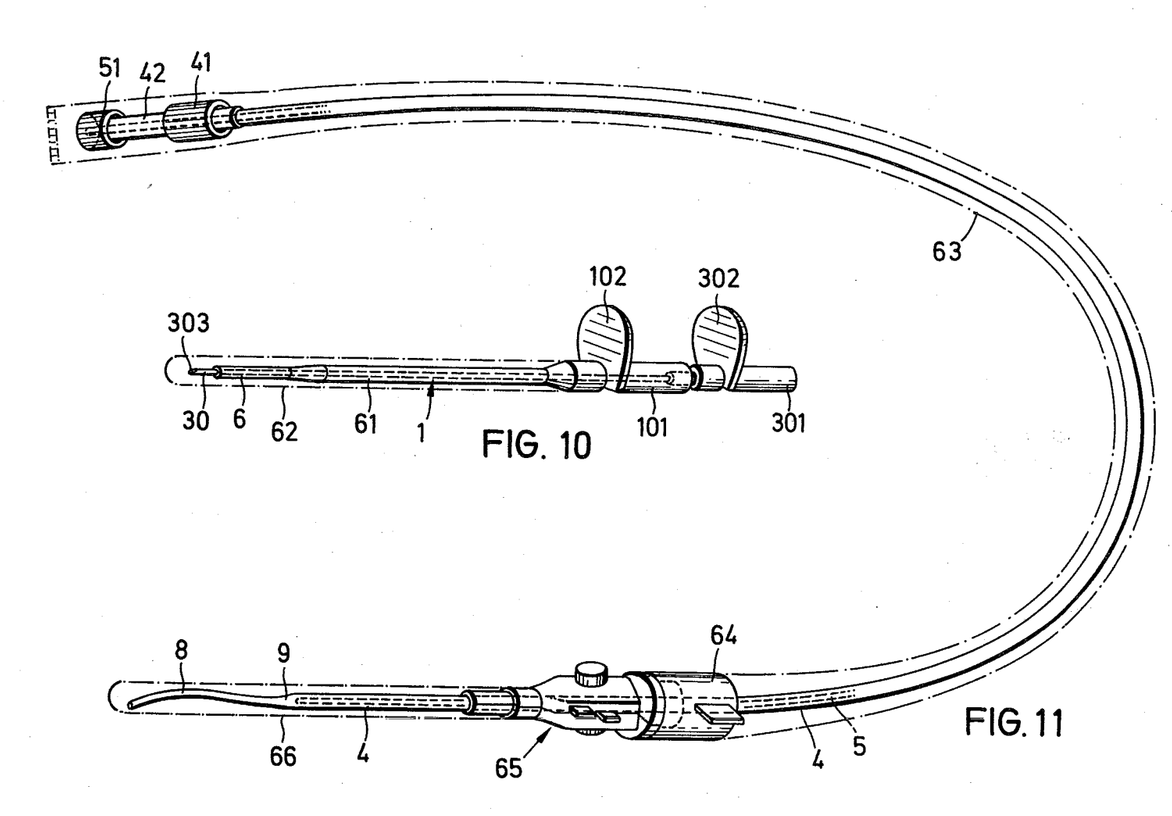
FIGS. 10 and 11 illustrate a complete catheter set with FIG. 10 showing an insertion tube having a canula inside and FIG. 11 showing the catheter containing a mandrin.

FIG. 10 shows a canula 30 consisting of a steel tube, the rear end of which has a tubular plastic extension 301 with a projecting handle 302. The front end 303 of the canula 30 is ground obliquely to puncture the skin. The catheter insertion tube 1 is slipped over the canula 30. The front end of said tube 1 has an expansible portion 6, the inner diameter of which corresponds to the outer diameter of the canula 30, and which is followed by and joined to a cylindrical portion 61 having a greater diameter. A tubular extension 101 of plastic is secured to the rear end of portion 61. Portion 61 includes a laterally projecting handle 102.

Canula 30 is introduced through the longitudinal bore of the plastic extension 101 and through the catheter insertion tube 1, and its front end protrudes from the catheter insertion tube. To avoid injuries, a tubular plastic cap 62 is provided which covers the front region of the canula 30 and the catheter insertion tube 1 and which is slipped clampingly over the front end of the catheter extension 101.

Catheter 4 with the inserted mandrin 5 is illustrated in FIG. 11. Catheter 4 consists of a tubular hose, the front end 8 of which has a smaller diameter. The bore or channel extending through the catheter 4 continues to the front end 8 by having a smaller diameter. In other words, the front end 8 of the catheter 4 is also hollow. The front end of the mandrin 5 introduced into the catheter 4 extends to point 9 where the tapered catheter section 8 begins.

At the rear end of the catheter 4, there is a plastic tubular connecting piece 42 on which a tubular coupling member 41 is axially rotated or pivoted. At the rear end of the mandrin 5, a connecting piece 51 is mounted which can be locked with the connecting piece 42 of the catheter 4 so that the rear ends of catheter 4 and mandrin 5 can be fixed relative to each other.

Catheter 4 is enclosed by a protective hose 63 of a transparent thin plastic film to ensure the sterility of the catheter. At the front end of the protective hose 63, there is attached a tubular connecting piece 64, which is slipped over the rear end of an insertion piece 65. The insertion piece 65 consists of two halves hinge-connected at one longitudinal side and capable of being opened up. The catheter 4 is pushed through the insertion piece 65, while the protective hose 63 is flexibly folded together. According to FIG. 11, a plastic protective hood 66 is slipped over the front end of the insertion piece 65 to protect the front end of the catheter against contamination.

Figure 12:
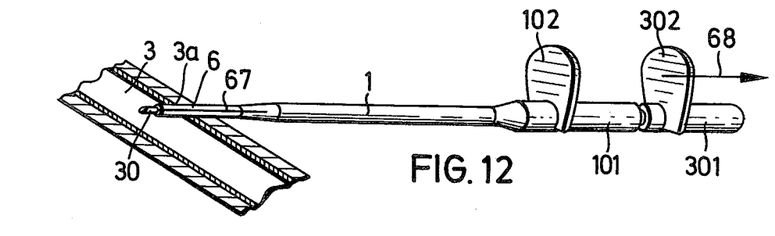
FIG. 12 shows the insertion tube-canula combination of FIG. 10 inserted in a blood vessel.

FIG. 12 shows the canula 30 with an insertion tube 1 slipped over it, while a blood vessel 3 is punctured. The insertion tube 1 consists of a thin-walled rigid plastic material. Region 6 of insertion tube 1 contains a longitudinal slot 67 thus permitting its subsequent expansion. After having punctured the blood vessel 3 by the canula with the insertion tube 1 in position thereon as shown in FIG. 12, the canula 30 is removed by withdrawing the handle 302 in the direction of arrow 68, while the insertion tube 1 maintains its position.

Figure 13:
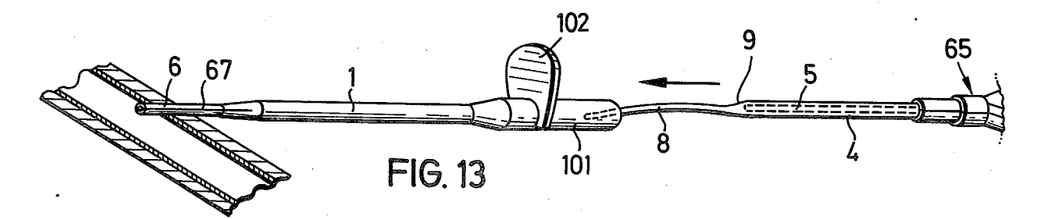
FIG. 13 shows the insertion tube in the blood vessel as shown in FIG. 12 but with the canula removed and the catheter containing the mandrin being inserted in the insertion tube.
Figure 14:
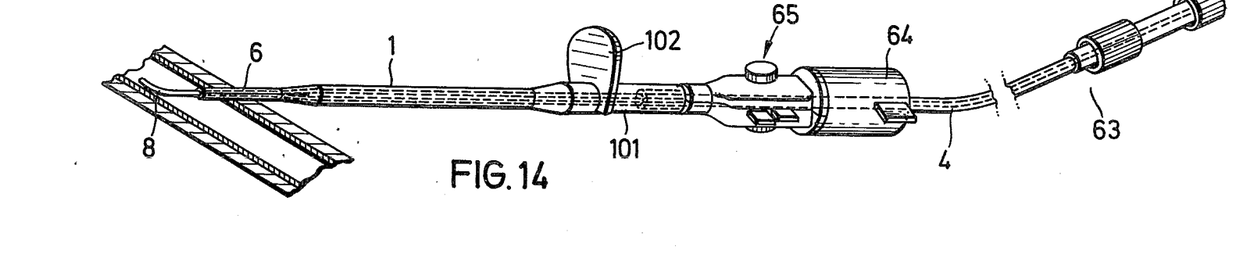
FIG. 14 shows the catheter front end advanced into the blood vessel from the position shown in FIG. 13.

As shown in FIGS. 13 and 14, catheter 4 containing mandrin 5 is then moved forward through the insertion piece 65 through the bore of the extension 101 into the insertion tube 1 until the soft front end 8 of the catheter penetrates the blood vessel, according to FIG. 14, and is guided by it. Then, the front end of the insertion piece 65 is introduced into the extension 101 of the insertion tube 1, as shown in FIG. 14, thus allowing the catheter 4 to slide forward in the insertion piece 65 and in the insertion tube 1 without being touched manually. The catheter 4 is advanced in that it is moved by seizing the insertion piece 65.

When point 9 of the catheter 4 moves into the tapered portion 6 of the insertion tube 1, the slot 67 is pressed apart. At the same time, the insertion tube 1 is removed according to FIG. 15, while the catheter is advanced further.

Figures 15, 16, 17:
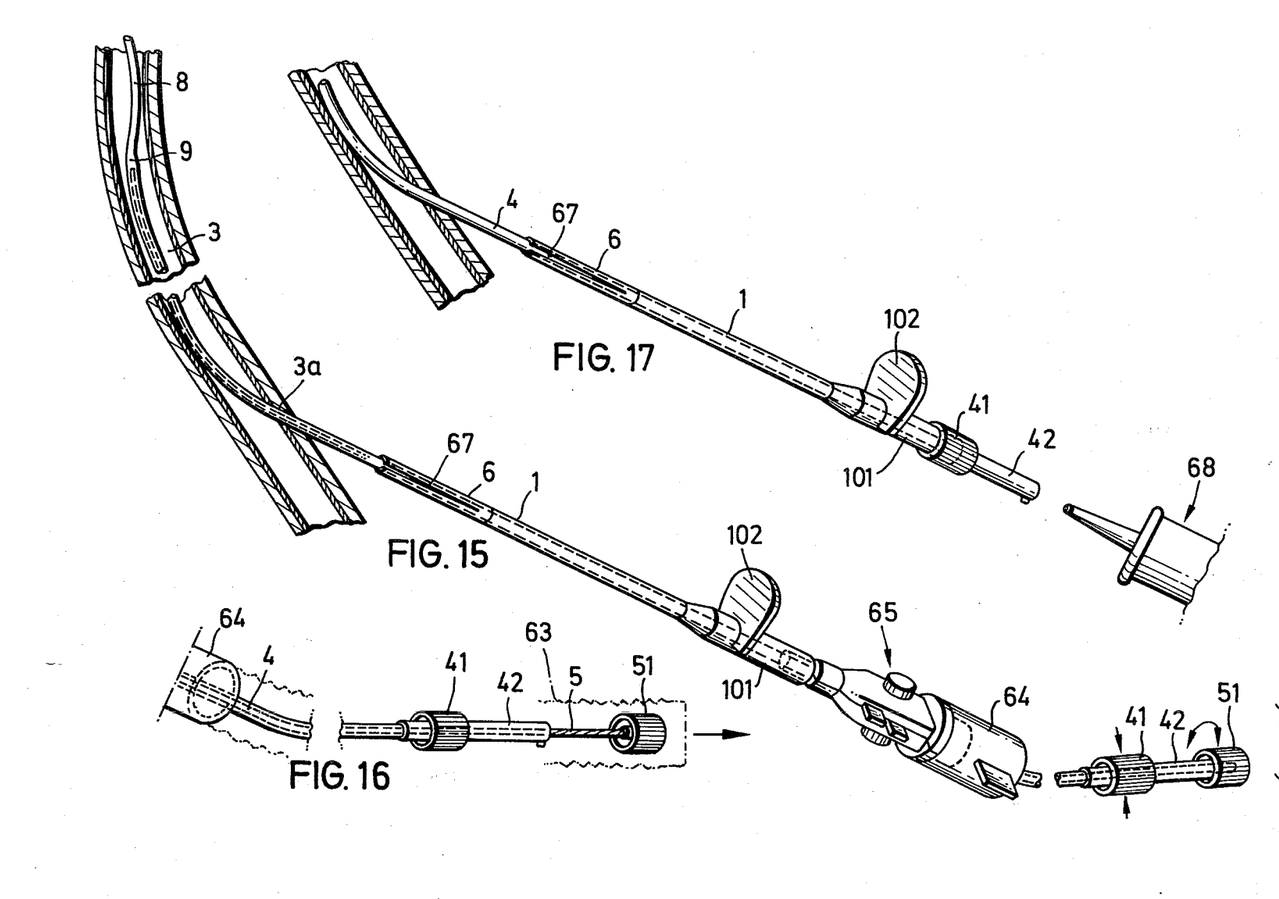
FIG. 15 shows the insertion tube tapered portion forced open along the slot therein by advancement of the catheter and the insertion tube withdrawn from the blood vessel.
FIG. 16 shows removal of the mandrin from the blood vessel.
FIG. 17 shows a syringe being attached to the catheter.

After the catheter 4 has been positioned in the blood vessel 3, the mandrin 5 is removed from the catheter 4 by pulling on the connecting piece 51. At the same time, the hose 63 with the ring 64 is withdrawn to the rear.

Then, according to FIG. 17, the rear end of the catheter 4 is joined with the rear end of the insertion tube 1 by rotating or screwing the coupling member 41 on the extension 101. Then, by inserting the front end of a syringe 68 into the extension 42, liquid can be injected into the catheter 4.

The foregoing detailed description has been given for clearness of understanding only, and no unnecessary limitations should be understood therefrom, as modifications will be obvious to those skilled in the art.

What is claimed is:

1. In a catheter set including a catheter and a catheter insertion tube into which the catheter to be inserted into a blood vessel is insertable, the improvement comprising:
    a catheter having an elongated soft and flexible front end portion with an external diameter smaller than the external diameter of the main body of the catheter;
    a catheter insertion tube having a front end portion with an internal diameter smaller than the external diameter of the main body of the catheter;
    the elongated smaller front end portion of the catheter being axially slidable in the catheter insertion tube front end portion so as to project partially out thereof without expanding the same; and
    the front end portion of the catheter insertion tube being expandable by movement of the catheter main body axially therein.

2. The improvement according to claim 1 in which the catheter main body external diameter is not less than the external diameter of the front end portion of the catheter insertion tube at a blood vessel puncture.

3. The improvement according to claim 1 in which the catheter insertion tube expandable front end comprises elastic material.

4. The improvement according to claim 1 in which the catheter insertion tube expandable front end has a longitudinal dividable area parallel to the tube axis.

5. The improvement according to claim 1 including a mandrin having an outer diameter not larger than the internal diameter of the catheter insertion tube front end portion internal diameter.

6. In a catheter set comprising a puncturing canula, a catheter and a catheter insertion tube into which tube said catheter to be inserted into a blood vessel is insertable, the improvement comprising:
    a catheter with a reduced insertion end; and
    a catheter insertion tube having a dilatable elastic area along at least a portion of its length permitting expansion of the tube dilatable area by insertion said catheter into the tube to expand the catheter insertion tube and permitting removal of the tube from the blood vessel over the catheter so that enlargement of the blood vessel puncture is substantially eliminated so it can be tightly sealed by inserting the catheter into the puncture; said catheter having a body with an end projection, at least as long as the catheter insertion tube, with an outer diameter smaller than the catheter insertion tube inner diameter and with the catheter body outer diameter at least as large as the catheter insertion tube outer diameter at the puncture.

7. The improvement according to claim 6 in which the catheter insertion tube has a discreet dilatable area over its entire length.

8. The improvement according to claim 7 in which the dilatable area consists of elastic material.

9. The improvement according to claim 7 in which the dilatable area includes zones of reduced strength.

10. The improvement according to claim 7 in which the dilatable area is a longitudinal dividable area parallel to the tube axis.

11. The improvement according to claim 10 in which the dividable area includes longitudinal slits.

12. The improvement according to claim 11 in which the dividable area includes overlapping step-like portions.

13. The improvement according to claim 6 in which the projection is tubular and has a uniform diameter.

14. The improvement according to claim 13 in which the opening in the projection is equal in diameter to the catheter opening.

15. The improvement according to claim 6, 13 or 14 in which the projection is at least as long as the catheter insertion tube.

* * * * *